United States Patent [19]
Kilmer

[11] Patent Number: 5,665,601
[45] Date of Patent: Sep. 9, 1997

[54] AVOIDING BUBBLE FORMATION WHILE SENSING AIR-LIQUID INTERFACE USING PRESSURIZED AIR FLOW

[75] Inventor: Kathleen Ellen Kilmer, Penfield, N.Y.

[73] Assignee: Johnson & Johnson Clinical Diagnostics, Inc., Rochester, N.Y.

[21] Appl. No.: 589,749

[22] Filed: Jan. 22, 1996

[51] Int. Cl.[6] .................................................. G01N 35/10
[52] U.S. Cl. .......................... 436/54; 436/43; 436/49; 436/180; 422/67; 422/100; 422/106; 422/112; 73/864.24; 73/864.25
[58] Field of Search ...................... 436/43, 49, 50, 436/54, 180; 422/63, 67, 100, 105, 106, 112; 73/864.24, 864.25

[56] References Cited

U.S. PATENT DOCUMENTS

| | | | |
|---|---|---|---|
| 4,794,085 | 12/1988 | Jessop et al. | 436/54 |
| 5,013,529 | 5/1991 | Itoh | 422/100 |
| 5,143,849 | 9/1992 | Barry et al. | 436/50 |
| 5,158,748 | 10/1992 | Obi et al. | 422/100 |
| 5,312,757 | 5/1994 | Matsuyama et al. | 436/54 |

*Primary Examiner*—Long V. Le
*Attorney, Agent, or Firm*—Dana M. Schmidt

[57] ABSTRACT

An aspirator/dispenser of liquid has a sensor for sensing contact with the liquid by the dispense vessel, which uses constant pressure air expelled out the tip of the dispense vessel. The sensor is improved in that the line of air pressure feeding into the vessel is vented in parallel with the vessel, to the atmosphere, so that the spike of pressure occurring when the vessel encounters the liquid, is released out the vent, rather than the vessel, thus avoiding bubble formation in the liquid.

8 Claims, 3 Drawing Sheets

1

AVOIDING BUBBLE FORMATION WHILE SENSING AIR-LIQUID INTERFACE USING PRESSURIZED AIR FLOW

FIELD OF THE INVENTION

This invention relates to an aspirator/dispenser having a liquid interface detector, and an improvement therefor that avoids creating entrapped air bubbles in the liquid.

BACKGROUND OF THE INVENTION

It is known to detect the contact of an aspirator tip by the liquid into which the tip is lowered for purposes of aspiration. A highly preferred method is by expelling pressurized air of constant pressure out of the tip orifice, the pressure inside the tip being detected by a pressure detector or transducer. When the latter detects an increase in pressure due to liquid encounter, the source of pressurized air is shut off from the tip, and the tip can then be evacuated in a conventional manner by a pump, to aspirate the liquid prior to dispensing it elsewhere. A representative patent depicting this arrangement is U.S. Pat. No. 5,013,529, especially FIG. 3 thereof.

With such a mechanism, there is a disadvantage: the shut-off valve disconnecting the tip from the pressurized source is unable to always prevent such a build-up of pressure as will cause one or more bubbles of variable size to be expelled from the tip into the liquid covering the tip orifice. Such bubbles are undesirable, because unless they disperse completely, they can be aspirated back into the tip in place of liquid volume, thus destroying the accuracy of the volume of liquid that is expected. More specifically: the system uses a pressure transducer to detect a spike of increased pressure representing the wall of liquid now blocking the tip orifice. The spike of pressure is essential for the transducer to work. Unfortunately, it is this spike which then creates an air bubble at the tip orifice. The bubble at best sits at the tip orifice, only to be aspirated in during the aspiration cycle of the tip. In such a case, the air bubble volume becomes part of, and affects, only the residual volume of the tip and is never "dispensed". As such, then, such a bubble creates a second order effect by effectively changing the dead air volume in the air displacement system. For example, if the bubble volume represents 10% of an aspirated aliquot of liquid, its effect on what is subsequently dispensed is perhaps only about 2%.

The situation is worse, however, if the bubble disassociates from the tip, which happens on occasion. Then, the bubble could be aspirated back into the tip as part of the "slug" of volume that is to be dispensed. The bubble will migrate into the residual volume. However, timing is such that this migration is not always completed before the dispense operation (depending on the fluid properties of the sample and the initial location of the bubble). In that case, the bubble creates a first order error—a bubble volume representing 10% of the dispensed aliquot volume ends up as a 10% error in that dispensed aliquot.

In either case, either error is not acceptable for precise metering modes.

The problem cannot be solved merely by reducing the total pressure $P_T$ of the compressed air source of air pressure that is being expelled, with the intent of having less pressure build-up in the tip at the time of disconnect of the source of air pressure. The spike of pressure $\Delta P_1$ is still needed within the tip to trigger the pressure detector to cause the disconnect. Thus, even if the $P_T$ of the source of air is reduced by half, so that the spike pressure $\Delta P_2$ is, for example, only one half of the spike $\Delta P_1$ that occurs for disconnect in the apparatus of said '529 patent, that is still enough pressure to cause a bubble to be ejected from the tip into the liquid. Because no such bubbles can be tolerated, even simply reducing by half the $P_T$ of the pressurized air source, is not an adequate solution. Furthermore, any attempt to greatly reduce the pressure spike that triggers the detector, to reduce the bubble size, quickly reaches a limit imposed by the signal-to-noise ratio required for a detectable spike.

SUMMARY OF THE INVENTION

I have determined that the solution to the problem requires an instantaneous release of pressure build-up within the tip at the time of contact with the liquid interface, through an outlet other than the tip orifice. I have provided apparatus and a method for accomplishing this.

More specifically, in accord with one aspect of the invention, there is provided an aspirator and dispenser for use in an analyzer, comprising a source of pressurized air; a liquid-collecting and holding vessel fluidly connected to the source, the vessel including an aspirating orifice; means for lowering the vessel while fluidly connected to the source, into a container of liquid to be aspirated; terminating means for terminating the flow of the pressurized air to the vessel upon build-up of pressure within the vessel due to encounter with the liquid; and a vent means for venting the vessel of the pressurized air at an outlet other than the orifice, the vent being connected in parallel to the vessel, downstream from the terminating means and in a position effective to vent pressure from the vessel when pressure build-up occurs within the vessel because of blockage of the orifice, so that pressurized air in the vessel is vented by the vent when the orifice is blocked by liquid, rather than forming bubbles in the liquid in the container.

In accord with another aspect of the invention, there is provided a method of sensing the presence of an air-liquid interface by an aspirator/dispenser having a vessel lowered to and into a liquid forming the interface, the method comprising the steps of a) pressurizing the aspirator/dispenser vessel while lowering the vessel, b) detecting pressure levels in the vessel during the step a), and c) terminating Step a) when a pressure build-up representative of encounter of the vessel with the interface occurs. The method is improved in that the steps a) and b) include the step of venting the aspirator/dispenser to the atmosphere at an outlet separate from the vessel while lowering the vessel, so that when the pressure build-up occurs, excess pressure is released from the vessel instantly while step c) is occurring so that no bubbles are expelled into the liquid because of excess pressure.

Therefore, it is an advantageous feature of the invention that an air-liquid interface can be sensed by an aspirator tip using pressurized air, without forming bubbles in the liquid to be aspirated.

Other advantageous features will become apparent upon reference to the Detailed Description that follows, when read in light of the attached drawings.

DESCRIPTION OF THE PREFERRED EMBODIMENTS

The invention is described in connection with certain preferred embodiments, in which a particular constant pressure is generated by a compressed air source, and a pressure spike is detected when the fluid interface is encountered, using a particular pressure transducer. In addition, the invention is useful regardless of the air pressure used for sensing, whether or not the air pressure is from a compressed air source, whether or not a particular pressure transducer is used, and regardless of the type of liquids sensed, so long as the sensor is separately vented to the atmosphere apart from the vessel orifice to be used for aspiration.

Figure 1:
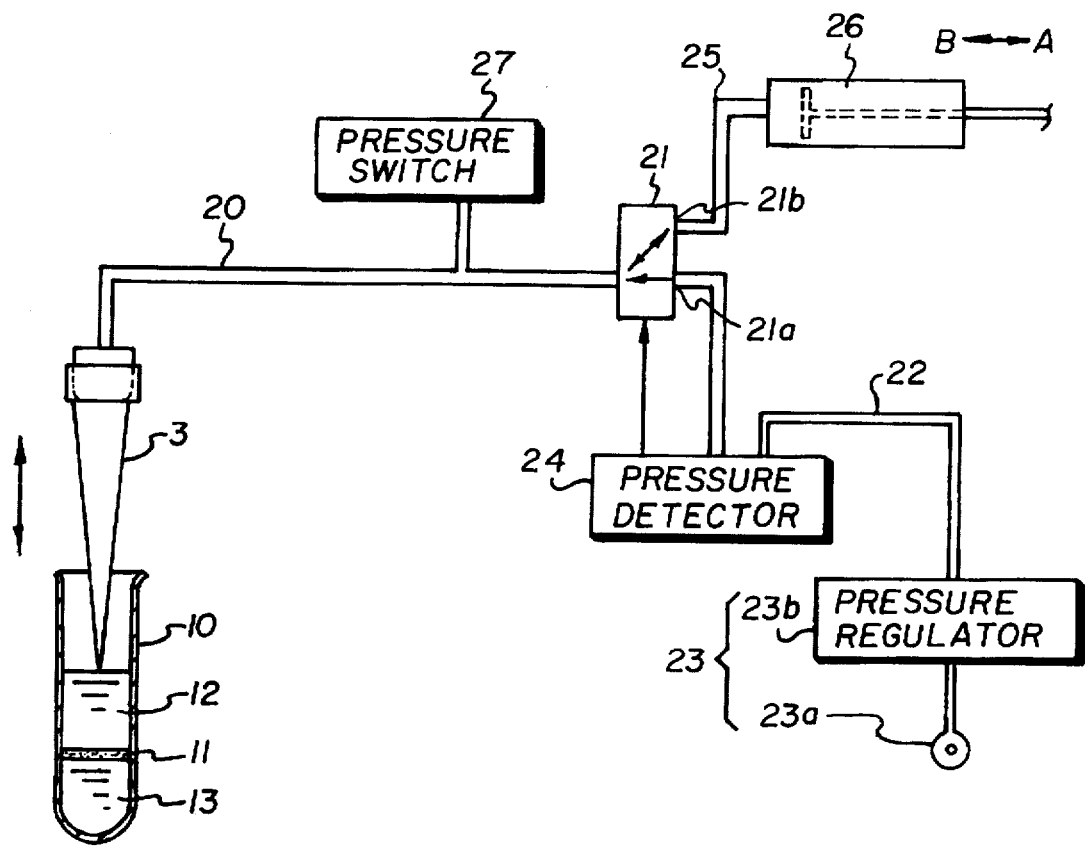
FIG. 1 is a schematic illustration of the prior art air-liquid interface detector apparatus using pressurized air.

FIG. 1 illustrates the prior art method noted above. A source of constant pressure air is provided at 22, and delivered via a regulator 23b and a pressure detector 24 to a three-way valve 21 responsive to pressure detector 24. Valve 21 is initially connected to vessel 3 as it is lowered toward liquid 12. When it contacts the liquid, a pressure spike occurs in vessel 3 and is detected by detector 24. In response, valve 21 switches over so that constant pressure from line 22 is no longer applied, and vessel 3 is instead connected to piston pump 26 for aspirating liquid into vessel 3.

However, the spike of pressure that triggers detector 24 has nowhere to go except out the tip orifice of vessel 3, thus creating the air bubble(s) noted above to be the problem.

The Invention

The solution is to add an atmospheric vent line to line 20 through a valve that is normally open during the search for the fluid interface, but which closes after the air pressure line (22 in FIG. 1) is disconnected from the vessel.

Figure 2:
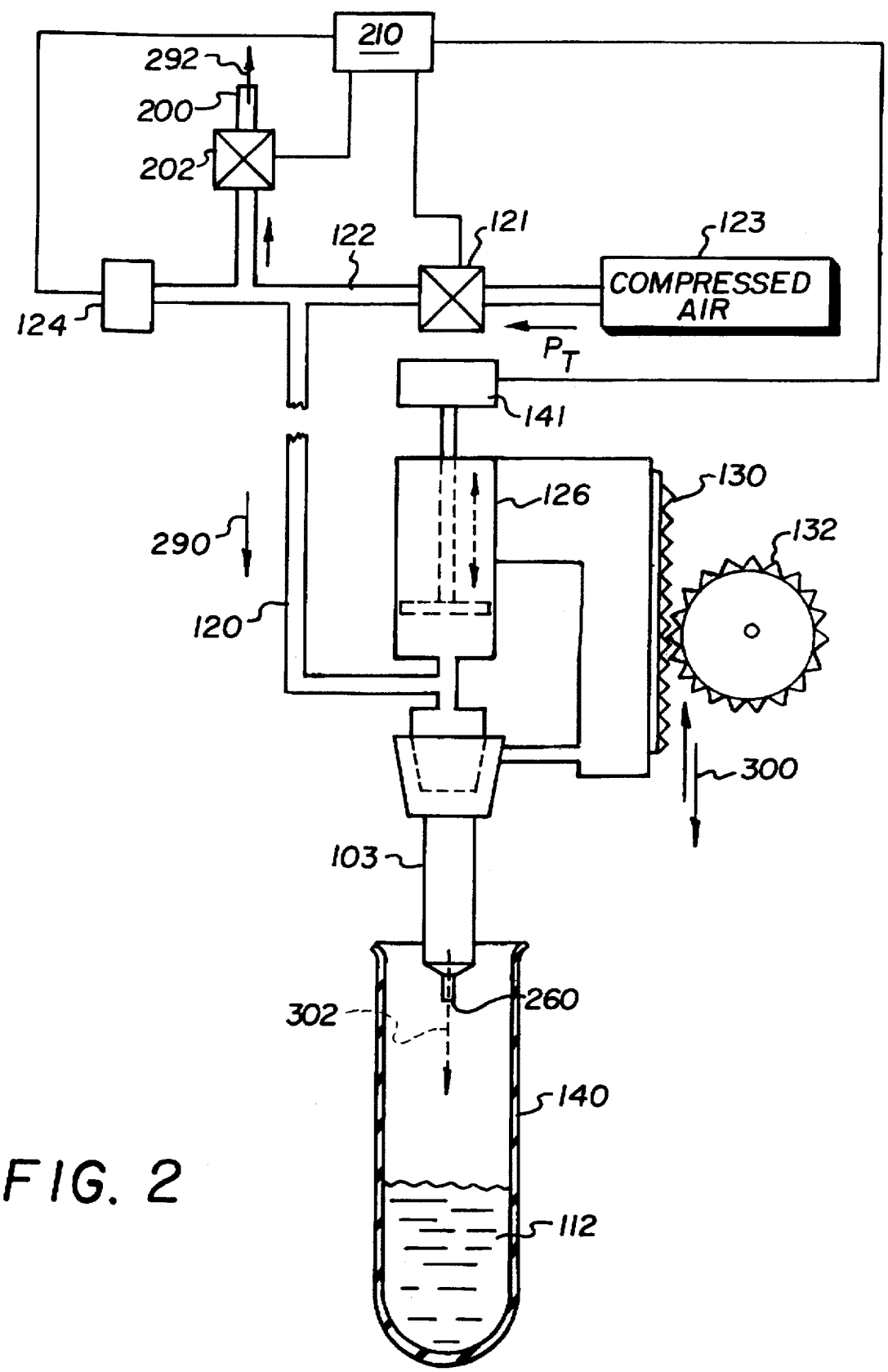
FIG. 2 is a schematic illustration of the detector apparatus constructed in accordance with the invention.

In terms of a preferred construction, FIG. 2, a tip or vessel 103 is raised or lowered while it is connected to a line 120, which is connected to a pressure transducer detector 124 and a line 122 receiving a source of constant air pressure from a source such as compressed air 123, through valve 121 that is normally open as vessel 103 advances towards fluid such as serum 112 in container 140. (Any mechanism can be used to raise and lower vessel 103, for example a rack 130 and a driven pinion gear 132.) Once fluid 112 is contacted by vessel 103, a conventional piston pump 126 can be operated by, e.g., a stepper motor 141, to aspirate liquid into vessel 103, and then to dispense the aspirated liquid onto, e.g. a slide test element, or into another container (neither of which is shown).

What is added by the invention, is vent line 200 connected in parallel to vessel 103, by valve 202 connected to line 122, which is also connected to transducer 124. Valve 202 is left open during liquid level sensing only. Vent line 200 exits to the atmosphere. Valves 202 and 121 are in turn connected to a conventional controller 210, which operates the valves in response to transducer 124, which can be, for example, a strain gauge silicon diaphragm relative pressure sensor.

In operation, the pressure $P_T$ of compressed air source 123 is delivered via valve 121 to both lines 120 and 200 (arrows 290 and 292) while vessel 103 is lowered, arrow 300, towards serum 112. Air expelled from tip orifice 260 of vessel 103, arrow 302, when it encounters serum 112, creates a spike of pressure in excess of $P_T$, a spike that triggers transducer 124. This trigger sends a signal via controller 210 to shut off valve 121, removing the air pressure $P_T$ from entering further into line 120 and vessel 103. As a result, the air pressure in line 120 and vessel 103 above ambient, and specifically the triggering spike of pressure, is instantly released out through valve 202 and vent 200, arrow 292, instead of out vessel 103 into liquid 112. Shortly thereafter, for example 30 milliseconds, controller 210 shuts off valve 202 and activates motor 140, preferably after a pause, to cause pump 126 to aspirate some of serum 112 into vessel 103, without any air bubbles. (Vessel 103 is gradually lowered as liquid 112 is aspirated out of container 140.)

Figure 3:
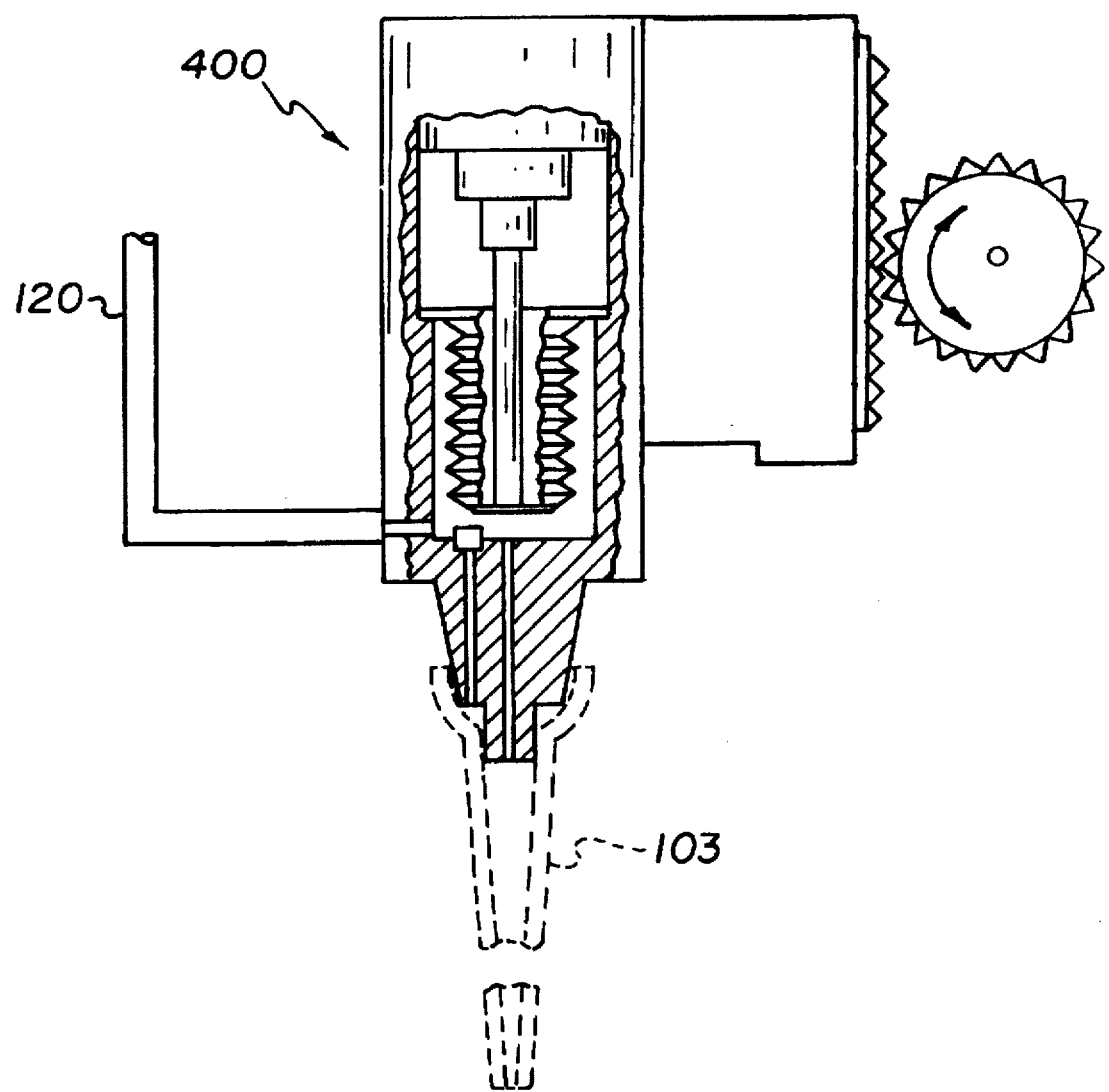
FIG. 3 is a fragmentary, partially sectioned vertical elevational view of an alternative embodiment of the invention.

Alternatively, FIG. 3, pump 126 can be replaced by a conventional bellows pump 400, for example, that which is shown in U.S. Pat. No. 4,852,620 issued on Aug. 1, 1989, to aspirate and dispense liquid into and from vessel 103 by creating, as is conventional, a partial vacuum and a partial pressure, respectively. The details of the bellows pump as described in said '620 patent are expressly incorporated herein by reference.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. An aspirator and dispenser for use in an analyzer, comprising a source of pressurized air; a liquid-collecting and holding vessel fluidly connected to said source, said vessel including an aspirating orifice; means for lowering said vessel while fluidly connected to a flow of pressurized air from said source, into a container of liquid to be aspirated; terminating means for terminating the flow of said pressurized air to said vessel upon build-up of pressure within said vessel due to encounter with the liquid; and a vent for venting said vessel of said pressurized air at an outlet other than said orifice, said vent being connected in parallel to said vessel, downstream from said terminating means and in a position effective to vent pressure from said vessel when pressure build-up occurs within said vessel because of blockage of said orifice by the liquid;

so that pressurized air in said vessel is vented by said vent when said orifice is blocked by liquid, rather than forming bubbles in the liquid in the container.

2. An aspirator and dispenser as defined in claim 1, wherein said source of pressurized air comprises means for supplying compressed air at a constant pressure.

3. An aspirator and dispenser as defined in claim 1, and further including pump means for generating a partial vacuum and a partial pressure within said vessel for aspirating and dispensing, respectively, liquid into or out of said vessel, and further including a valve for closing off said vent when operating said pump means.

4. An aspirator and dispenser as defined in claim 3, wherein said pump means comprises a piston pump.

5. An aspirator and dispenser as defined in claim 3, wherein said pump means comprises a bellows pump.

6. An aspirator and dispenser as defined in claim 1, wherein said vent is constantly open during liquid level sensing.

7. In a method of sensing the presence of an air-liquid interface by an aspirator/dispenser having a vessel lowered to and into a liquid forming said interface, the method comprising the steps of a) pressurizing said aspirator/dispenser vessel while lowering said vessel, b) detecting pressure levels in said vessel during said step a), and c) terminating said step a) when a pressure build-up representative of encounter of said vessel with said interface occurs, the improvement wherein said steps a) and b) include the step of venting said aspirator/dispenser to the atmosphere at an outlet separate from said vessel while lowering said vessel, so that when said pressure build-up occurs, excess pressure is released from said vessel instantly while step c) is occurring so that no bubbles are expelled into the liquid because of excess pressure.

8. A method as defined in claim 7, and further including the steps of terminating said venting after said excess pressure is released, and aspirating liquid into said vessel thereafter.

* * * * *